United States Patent
Shin et al.

(10) Patent No.: US 11,345,660 B2
(45) Date of Patent: May 31, 2022

(54) METHOD FOR PREPARING INTERMEDIATE OF 4-METHOXYPYRROLE DERIVATIVE

(71) Applicant: Daewoong Pharmaceutical Co., Ltd., Gyeonggi-do (KR)

(72) Inventors: Jeong-Taek Shin, Gyeonggi-do (KR); Jeong-Hyun Son, Gyeonggi-do (KR); Seung Chul Lee, Gyeonggi-do (KR)

(73) Assignee: DAEWOONG PHARMACEUTICAL CO., LTD., Gyeonggi-Do (KR)

( * ) Notice: Subject to any disclaimer, the term of this patent is extended or adjusted under 35 U.S.C. 154(b) by 277 days.

(21) Appl. No.: 16/608,924

(22) PCT Filed: Jun. 21, 2018

(86) PCT No.: PCT/KR2018/006989
§ 371 (c)(1),
(2) Date: Oct. 28, 2019

(87) PCT Pub. No.: WO2018/236153
PCT Pub. Date: Dec. 27, 2018

(65) Prior Publication Data
US 2020/0181080 A1    Jun. 11, 2020

(30) Foreign Application Priority Data

Jun. 21, 2017 (KR) .................. 10-2017-0078745

(51) Int. Cl.
*C07D 207/36* (2006.01)
(52) U.S. Cl.
CPC .................. *C07D 207/36* (2013.01)
(58) Field of Classification Search
CPC .................. C07D 207/36; C07D 207/38
See application file for complete search history.

(56) References Cited

U.S. PATENT DOCUMENTS

| | | | |
|---|---|---|---|
| 8,048,909 B2 | 11/2011 | Kajino et al. | |
| 8,338,461 B2 | 12/2012 | Kajino et al. | |
| 8,604,061 B2 | 12/2013 | Galley et al. | |
| 10,100,010 B1 | 10/2018 | Lee et al. | |
| 10,336,695 B2* | 7/2019 | Kim ................ | A61K 31/40 |
| 10,487,053 B2* | 11/2019 | Kim ................ | C07C 55/10 |
| 10,683,268 B2 | 6/2020 | Kim et al. | |
| 10,710,961 B2* | 7/2020 | Shin ................ | C07D 207/36 |
| 10,889,545 B2* | 1/2021 | Kim ................ | A61P 1/04 |
| 10,913,715 B2* | 2/2021 | Kim ................ | C07D 207/48 |
| 2011/0059940 A1 | 3/2011 | Gilligan et al. | |
| 2020/0181079 A1* | 6/2020 | Shin ................ | C07D 207/36 |
| 2021/0139424 A1 | 5/2021 | Kim et al. | |
| 2021/0221770 A1* | 7/2021 | Shin ................ | A61P 1/00 |

FOREIGN PATENT DOCUMENTS

| | | | | |
|---|---|---|---|---|
| CL | 2019003449 A1 | 3/2020 | | |
| EA | 29788 B1 | 5/2018 | | |
| EP | 714895 A1 | 6/1996 | | |
| EP | 1803709 A1 | 7/2007 | | |
| JP | 2010-517953 A | 5/2010 | | |
| JP | 2011-523633 A | 8/2011 | | |
| KR | 10-1613245 B1 | 4/2016 | | |
| RU | 95121094 | 11/1997 | | |
| RU | 2415838 C2 | 4/2011 | | |
| WO | WO-2006/036024 A1 | 4/2006 | | |
| WO | WO-2010038948 A2 * | 4/2010 | ........ | C07D 207/36 |
| WO | WO-2016/175555 A2 | 11/2016 | | |
| WO | WO-2016175555 A2 * | 11/2016 | ........ | A61P 31/04 |
| WO | WO-2017/164575 A1 | 9/2017 | | |
| WO | WO-2017164575 A1 * | 9/2017 | ........ | C07C 55/10 |
| WO | WO-2018/221971 A1 | 12/2018 | | |

OTHER PUBLICATIONS

U. Grošelj et al., 69 Tetrahedron, 11092-11108 (2013) (Year: 2013).*
B. Khalili et al., 73 Journal of Organic Chemistry, 2090-2095 (2008) (Year: 2008).*
S. Gupta, Synthesis, 726-727 (1975) (Year: 1975).*
A. San Feliciano et al., 45 Tetrahedron, 6553-6562 (1989) (Year: 1989).*
Notice of Allowance in JP Application No. 2019-563427 dated Nov. 10, 2020, 3 pages.
Office Action in CL Application No. 201903450 dated Nov. 30, 2020, 12 pages.
Grošelj et al., "α-Amino Acid Derived Enaminones and Their Application in the Synthesis of N-protected Methyl 5-substituted-4-hydroxypyrrole-3-carboxylates and Other Heterocycles", Tetrahedron, vol. 69, 2013, p. 11092-11108.

(Continued)

*Primary Examiner* — Alexander R Pagano
(74) *Attorney, Agent, or Firm* — White & Case LLP

(57) ABSTRACT

The present invention relates to a method for preparing intermediates of 4-methoxypyrrole derivatives. The preparation method according to the present invention has advantages that the production cost can be lowered by using inexpensive starting materials, a high-temperature reaction is not required as a whole, inexpensive and non-explosive reagents are used instead of (trimethylsilyl)diazomethane, and further an intermediate of 4-methoxypyrrole derivatives can be prepared as a whole at a high yield.

17 Claims, No Drawings

(56) References Cited

OTHER PUBLICATIONS

Ričko et al., "Organocatalyzed Deracemization of $\Delta^2$-Pyrrolin-4-ones", Advanced Synthesis & Catalysis, vol. 359, Jun. 8, 2017, pp. 2288-2296.
Campaigne et al., "Synthesis of Some 5-Aryl-2,2'-dipyrromethenes as Analogs of Prodigiosin (1)", Journal of Heterocyclic Chemistry, vol. 13, Issue 3, 1976, pp. 497-503.
Search Report and Written Opinion in International Application No. PCT/KR2018/006989 dated Sep. 27, 2018, 10 pages.
Office Action in RU Application No. 2019135250 dated May 25, 2020, 14 pages.

\* cited by examiner

METHOD FOR PREPARING INTERMEDIATE OF 4-METHOXYPYRROLE DERIVATIVE

TECHNICAL FIELD

The present invention relates to a method for preparing intermediates used in the preparation of 4-methoxypyrrole derivatives.

BACKGROUND OF ART

Gastrointestinal track ulcers, gastritis, and reflux esophagitis occur while the balance between aggressive factors (e.g., gastric acid, *Helicobacter pylori* pepsin, stress, alcohol and tobacco) and protective factors (e.g., gastric mucosa, bicarbonate, prostaglandins, the degree of blood supply, etc.) is destroyed. Therefore, a therapeutic agent for gastrointestinal damage such as gastrointestinal track ulcer, gastritis and reflux esophagitis is divided into a drug for inhibiting the aggressive factors and a drug for enhancing the protective factors.

Meanwhile, it is reported that gastrointestinal track ulcers, gastritis and reflux esophagitis occur ulcers even without an increase in secretion of gastric acid. Thus, as much as the aggressive factor increases, a reduction in protective factors due to a pathological change of the gastric mucosa is thought to play an important role in the occurrence of gastric ulcers. Therefore, in addition to drugs for inhibiting the aggressive factor, drugs for enhancing the protective factors are used for the treatment of gastrointestinal ulcer and gastritis. As the drugs for enhancing protective factors, mucosal protective drugs which are attached to the ulcer site to form a physicochemical membrane, drugs that promote the synthesis and secretion of mucus have been known.

On the other hand, *Helicobacter pylori* (*H. pylori*), which is a bacteria present in the stomach, has been known to cause chronic gastritis, gastric ulcer, duodenal ulcer and the like, and a number of patients with gastrointestinal damages are infected with *H. pylori*. Therefore, these patients should take antibiotics such as clarithromycin, amoxicillin, metronidazole and tetracycline, together with anti-ulcer agents such as a proton pump inhibitor, or a gastric pump antagonist. Consequently, various side effects have been reported.

Therefore, there is a need to develop anti-ulcer drugs which inhibit the secretion of gastric acid (e.g., proton pump inhibitory activity) and enhance protective factors (e.g., an increase in mucus secretion) and at the same time have disinfectant activity against *H. pylori*.

In this connection, Korean Patent No. 10-1613245 discloses that a 4-methoxypyrrole derivative or a pharmaceutically acceptable salt thereof has excellent anti-ulcer activity (i.e., proton pump inhibitory activity, etc.) and disinfectant activity against *H. pylori*, and thus can be effectively used for the prevention and treatment of gastrointestinal damage due to gastrointestinal track ulcer, gastritis, reflux esophagitis or *Helicobacter pylori*.

In the preparation of the 4-methoxypyrrole derivative described in the above patent, the following compound is prepared as an intermediate.

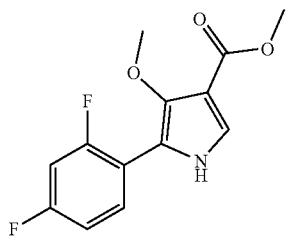 [SMILES: COC(=O)c1c[nH]c(-c2ccc(F)cc2F)c1OC]

According to the description of the above patent, the intermediate is prepared from 2,4-difluorophenylglycine, and the preparation method consists of four steps in total (Steps (8-1) to (8-3) of Example 8 described in Korean Patent No. 10-1613245). However, according to the preparation method of the above patent, the total yield is as low as 9.0%, a high-temperature reaction is required as a whole, and thus expensive equipment is required. Especially, (trimethylsilyl)diazomethane is used as a reactant, but this reagent is not only expensive but also explosive and thus is not suitable for industrial mass production.

Given the above circumstances, the present inventors have conducted intensive studies on a new preparation method capable of preparing the above intermediate. As a result, the inventors have found a preparation method in which a high-temperature reaction is not required as a whole as in the preparation method described later, and inexpensive, non-explosive reagent is used instead of (trimethylsilyl)diazomethane, and further, the yield is improved as a whole, thereby completing the present invention.

DETAILED DESCRIPTION OF THE INVENTION

Technical Problem

It is an object of the present invention to provide a method for preparing an intermediate which can be usefully used in the preparation of 4-methoxypyrrole derivatives.

Technical Solution

In order to achieve the above object, the present invention provides a preparation method as shown in the following Reaction Scheme 1, and more specifically, the preparation method comprises the steps of:

1) reacting a compound represented by the following Chemical Formula 1-1 with ammonium chloride, sodium cyanide, or potassium cyanide, followed by reaction with an acid to prepare a compound represented by the following Chemical Formula 1-2;

2) protecting a compound represented by the following Chemical Formula 1-2 with an amine protecting group (P) to prepare a compound represented by the following Chemical Formula 1-3;

3) reacting a compound represented by the following Chemical Formula 1-3 with (i) methylpotassium malonate or methylsodium malonate, (ii) carbonyldiimidazole, and (iii) magnesium halide, followed by reaction with an acid to prepare a compound represented by the following Chemical Formula 1-4;

4) reacting a compound represented by the following Chemical Formula 1-4 with N,N-dimethylformamide dimethylacetal to prepare a compound represented by the following Chemical Formula 1-5;

5) reacting a compound represented by the following Chemical Formula 1-5 with dimethyl sulfate to prepare a compound represented by the following Chemical Formula 1-6; and 6) reacting a compound represented by the following Chemical Formula 1-6 with an acid via deprotection to prepare a compound represented by the following Chemical Formula 1.

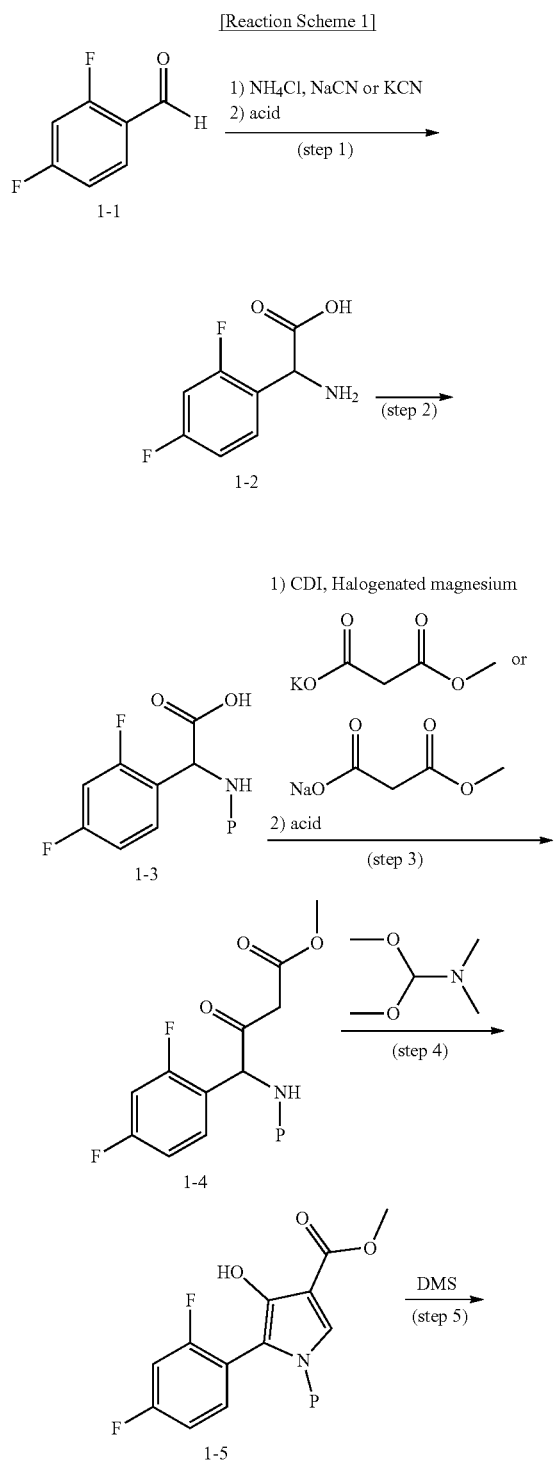

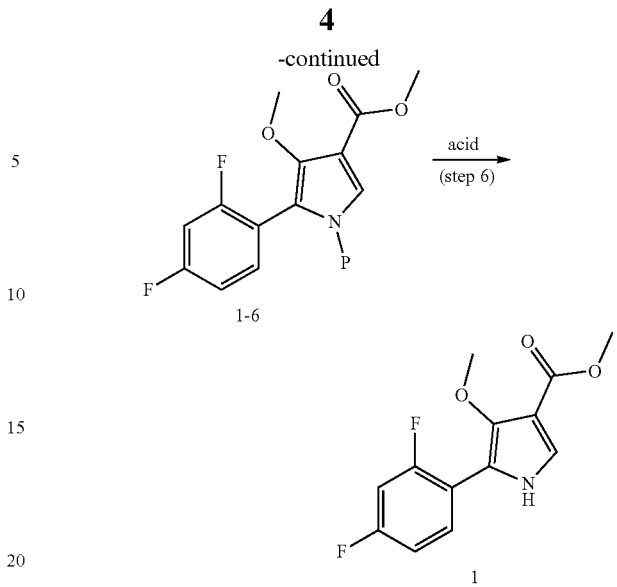

Hereinafter, the present invention will be described in detail for each step.

(Step 1)

The step 1 relates to Strecker amino acid synthesis, which is a step of preparing an amino acid like a compound represented by the Chemical Formula 1-2 from the Chemical Formula 1-1.

The reaction consists substantially of two reactions. First, the first reaction is to react a compound represented by the Chemical Formula 1-1 with ammonium chloride, and sodium cyanide, or potassium cyanide.

Preferably, the molar ratio of the compound represented by the Chemical Formula 1-1 to ammonium chloride is 10:1 to 1:10, more preferably 5:1 to 1:5, and most preferably 3:1 to 1:3. Preferably, the molar ratio of the compound represented by the Chemical Formula 1-1 to sodium cyanide or potassium cyanide is 10:1 to 1:10, more preferably 5:1 to 1:5, and most preferably 3:1 to 1:3.

Preferably, as a solvent for the first reaction, an alcohol having from 1 to 4 carbon atoms, and ammonium hydroxide or ammonium carbonate are used. More preferably, the alcohol having 1 to 4 carbon atoms is methanol, ethanol, propanol, iso-propanol, butanol, or tert-butanol.

Preferably, the first reaction is carried out at 0° C. to 40° C. When the reaction temperature is less than 0° C., there is a problem that the production yield is lowered. When the reaction temperature exceeds 40° C., the production yield does not substantially increase.

Preferably, the first reaction is carried out for 1 to 48 hours. When the reaction time is less than 1 hour, there is a problem that the reaction does not proceed sufficiently and thus the production yield is lowered. When the reaction time exceeds 48 hours, the production yield does not substantially increase.

On the other hand, after the first reaction is completed, a step of purifying the product may be included, if necessary. Preferably, the purification is carried out by crystallizing a cyanamide compound from the product of the reaction. As the crystallization solvent, water and an alcohol having 1 to 4 carbon atoms can be used. Preferably, the alcohol having 1 to 4 carbon atoms is methanol, ethanol, propanol, iso-propanol, butanol, or tert-butanol. Preferably, water is added to the reaction product and cooled to 10 to 15° C. Then, an alcohol having 1 to 4 carbon atoms is added thereto and stirred for 10 minutes to 2 hours.

After the first reaction is completed, a second reaction is carried out in which the product of the first reaction is reacted with an acid.

As the acid that can be used, acetic acid or hydrochloric acid can be mentioned. Preferably, acetic acid and hydrochloric acid are used together. The acid not only acts as a reactant in the second reaction, but also acts as a solvent. Therefore, it is preferable to use the acid in an amount sufficient to dissolve the first product.

Preferably, the second reaction is carried out at 80 to 120° C. When the reaction temperature is less than 80° C., there is a problem that the production yield is lowered. When the reaction temperature exceeds 120° C., the production yield does not substantially increase.

Preferably, the second reaction is carried out for 1 to 10 hours. When the reaction time is less than 1 hour, there is a problem that the reaction does not proceed sufficiently and thus the production yield is lowered. When the reaction time exceeds 10 hours, the production yield does not substantially increase.

On the other hand, after the second reaction is completed, a step of purifying the product may be included, if necessary.

(Step 2)

The step 2 is a step of protecting a compound represented by the Chemical Formula 1-2 with an amine protecting group (P), which is a step of preparing a compound represented by the Chemical Formula 1-3 by reacting a compound represented by the Chemical Formula 1-2 with a compound capable of introducing an amine protecting group (P).

Preferably, the amine protecting group (P) is tert-butoxycarbonyl (Boc), fluorenylmethyloxycarbonyl (Fmoc), Tosyl, or Acyl. In addition, the compound capable of introducing an amine protecting group (P) refers to various compounds used in the art for introducing the protecting group. For example, when the amine protecting group (P) is a tert-butoxycarbonyl (Boc), the compound capable of introducing the amine protecting group includes di-tert-butyl dicarbonate.

Preferably, the molar ratio of the compound represented by the Chemical Formula 1-2 to the compound capable of introducing the amine protecting group (P) is 10:1 to 1:10, and more preferably 3:1 to 1:5.

Preferably, the reaction is carried out in the presence of a base. As the base, triethylamine, diisopropylamine, diisopropylethylamine, potassium carbonate, potassium hydrogencarbonate, sodium carbonate, sodium hydrogencarbonate, sodium hydroxide, potassium hydroxide, lithium hydroxide, sodium methylate, potassium butyrate, or cesium carbonate can be used, and preferably, sodium hydrogencarbonate is used. Preferably, the molar ratio of the compound represented by the Chemical Formula 1-2 to the base is 1:1 to 1:10, and more preferably 1:1 to 1:5.

Preferably, as a solvent for the above reaction, water, tetrahydrofuran, dioxane, methylene chloride, butyl alcohol, tetrahydrofuran, or a mixture thereof may be used. Preferably, water and tetrahydrofuran are used together.

Preferably, the reaction is carried out at 10 to 40° C. When the reaction temperature is less than 10° C., there is a problem that the production yield is lowered. When the reaction temperature exceeds 40° C., the production yield does not substantially increase. More preferably, the reaction is carried out at 20 to 30° C.

Preferably, the above reaction is carried out for 1 to 48 hours. When the reaction time is less than 1 hour, there is a problem that the reaction does not proceed sufficiently and thus the production yield is lowered. When the reaction time exceeds 48 hours, the production yield does not substantially increase. More preferably, the reaction is carried out for 6 to 24 hours.

On the other hand, after the reaction is completed, a step of purifying the product may be included, if necessary.

(Step 3)

The step 3 is a reaction for substituting a carboxyl group of the compound represented by the Chemical Formula 1-3, wherein the reaction consists substantially of two reactions.

First, the first reaction is a reaction for preparing a compound of the following Chemical Formula, which is a magnesium salt of the compound represented by the Chemical Formula 1-4 to be prepared. The second reaction is a reaction for preparing the magnesium salt of the compound represented by the Chemical Formula 1-4 by dissociating the magnesium salt of the compound represented by the Chemical Formula 1-4.

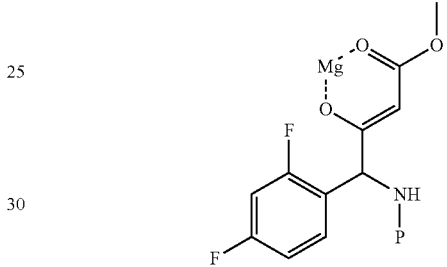

The compound represented by the Chemical Formula 1-4 is difficult to crystallize. Therefore, in the present invention, it is prepared by first preparing a magnesium salt thereof and then purifying it through crystallization.

First, the first reaction is a reaction of reacting a compound represented by the Chemical Formula 1-3 with (i) methylpotassium malonate or methylsodium malonate, (ii) carbonyldiimidazole, and (iii) magnesium halide. Preferably, as the magnesium halide, magnesium chloride or magnesium bromide may be used, and more preferably, magnesium chloride is used.

Preferably, the molar ratio of the compound represented by the Chemical Formula 1-3 to methylpotassium malonate or methylsodium malonate is 10:1 to 1:10, more preferably from 5:1 to 1:5, most preferably 3:1 to 1:3. Preferably, the molar ratio of the compound represented by the Chemical Formula 1-3 to carbonyldiimidazole is 10:1 to 1:10, more preferably 5:1 to 1:5, and most preferably 3:1 to 1:3. Preferably, the molar ratio of the compound represented by the Chemical Formula 1-3 to magnesium halide is 10:1 to 1:10, more preferably 5:1 to 1:5, and most preferably 3:1 to 1:3.

Preferably, the first reaction is carried out in the presence of triethylamine. Preferably, the molar ratio of the compound represented by the Chemical Formula 1-3 to triethylamine is 10:1 to 1:10, more preferably 5:1 to 1:5, and most preferably 3:1 to 1:3.

Preferably, as a solvent for the first reaction, acetonitrile or tetrahydrofuran is used, and more preferably, acetonitrile is used.

Preferably, the first reaction is carried out at 50 to 100° C. When the reaction temperature is less than 50° C., there is a problem that the production yield is lowered. When the reaction temperature exceeds 100° C., a side reaction occurs, which is not preferable.

Preferably, the first reaction is carried out for 10 minutes to 10 hours. When the reaction time is less than 10 minutes, there is a problem that the reaction does not proceed sufficiently and thus the production yield is lowered. When the reaction time exceeds 10 hours, a side reaction occurs, which is not preferable. More preferably, the reaction is carried out for 10 minutes to 5 hours.

After the first reaction is completed, a second reaction is performed in which the product of the first reaction is reacted with an acid.

As the acid that can be used, there may be mentioned hydrochloric acid, nitric acid, sulfuric acid, or phosphoric acid, preferably hydrochloric acid.

As the solvent for the second reaction, ethyl acetate, water, methylene chloride, or a mixture thereof may be used. Preferably, ethyl acetate and water are used together.

The second reaction is adjusted to pH 4 to 8 with an acid at 0 to 40° C. When the reaction temperature is less than 0° C. or higher than 40° C., there is a problem that the production yield is lowered. Preferably it is adjusted to pH 6 to 8. When the pH is 8 or more, the magnesium salt is not completely dissociated, and the production yield is lowered.

On the other hand, after the second reaction is completed, a step of purifying the product can be included, if necessary.

(Step 4)

The step 4 is a step of preparing a pyrrole derivative from a compound represented by the Chemical Formula 1-4, which is a step of reacting a compound represented by the Chemical Formula 1-4 with N,N-dimethylformamide dimethylacetal to prepare a compound represented by the Chemical Formula 1-5.

Preferably, the molar ratio of the compound represented by the Chemical Formula 1-4 to N,N-dimethylformamide dimethylacetal is 1:1 to 1:10, and more preferably 1:1 to 1:5.

Preferably, as a solvent for the reaction, toluene or xylene may be used, and more preferably, toluene is used.

Preferably, the reaction is carried out at 20 to 70° C. When the reaction temperature is less than 20° C., there is a problem that the production yield is lowered. When the reaction temperature exceeds 70° C., the production yield does not substantially increase.

Preferably, the reaction is carried out for 30 minutes to 12 hours. When the reaction time is less than 30 minutes, there is a problem that the reaction does not proceed sufficiently and thus the production yield is lowered. When the reaction time exceeds 12 hours, the production yield does not substantially increase.

On the other hand, since the compound represented by the Chemical Formula 1-5, which is a product of the reaction, is chemically unstable, it is preferable to continuously perform the subsequent reaction of step 5 without further purification.

(Step 5)

The step 5 is a reaction of substituting a hydroxy group of the compound represented by the Chemical Formula 1-5 with methoxy, which is a step of reacting a compound represented by the Chemical Formula 1-5 with dimethyl sulfate to prepare a compound represented by the Chemical Formula 1-6.

Preferably, the molar ratio of the compound represented by the Chemical Formula 1-5 to dimethyl sulfate is 10:1 to 1:10, more preferably from 5:1 to 1:5, most preferably from 3:1 to 1:3.

Further, the reaction is preferably carried out in the presence of a base. As the base, triethylamine, diisopropylamine, diisopropylethylamine, potassium carbonate, potassium hydrogencarbonate, sodium carbonate, sodium hydrogencarbonate, sodium hydroxide, lithium hydroxide, potassium hydroxide, sodium methylate, potassium butyrate, or cesium carbonate can be used, and preferably, potassium carbonate is used. In addition, the reaction can be carried out using methyl iodide in the presence of a base. Preferably, the molar ratio of the compound represented by the Chemical Formula 1-5 to the base is 1:1 to 1:5, and more preferably 1:1 to 1:3.

Preferably, as the solvent for the reaction, an alcohol having 1 to 4 carbon atoms or a ketone having 3 to 6 carbon atoms is used. More preferably, the solvent for the reaction is methanol, ethanol, propanol, butanol, tert-butanol, acetone, methyl ethyl ketone, or isobutyl ketone.

Preferably, the reaction is carried out at 20 to 60° C. When the reaction temperature is less than 20° C., there is a problem that the production yield is lowered. When the reaction temperature exceeds 60° C., a side reaction occurs, which is not preferable.

Preferably, the reaction is carried out for 1 to 24 hours. If the reaction time is less than 1 hour, there is a problem that the reaction does not proceed sufficiently and thus the production yield is lowered. When the reaction time exceeds 24 hours, a side reaction occurs, which is not preferable.

On the other hand, after the reaction is completed, a step of purifying the product may be included, if necessary.

(Step 6)

The step 6 is a step of removing a protecting group of the compound represented by the Chemical Formula 1-6, which is a step of reacting the compound represented by the Chemical Formula 1-6 with an acid to prepare a compound represented by the Chemical Formula 1.

As the acid that can be used, there may be mentioned trifluoroacetic acid, hydrochloric acid, nitric acid, sulfuric acid, or phosphoric acid, preferably trifluoroacetic acid.

Preferably, the molar ratio of the compound represented by the Chemical Formula 1-6 to the acid is 1:1 to 1:30, and more preferably 1:5 to 1:20.

Preferably, as a solvent for the reaction, methylene chloride, ethyl acetate, methanol, toluene, diethyl ether, tetrahydrofuran, or water may be used, and preferably, methylene chloride is used.

Preferably, the reaction is carried out at 10 to 40° C. If the reaction temperature is less than 10° C., there is a problem that the production yield is lowered. If the reaction temperature exceeds 40° C., a side reaction occurs, which is not preferable.

Preferably, the reaction is carried out for 1 to 24 hours. When the reaction time is less than 1 hour, there is a problem that the reaction does not proceed sufficiently and thus the production yield is lowered. When the reaction time exceeds 24 hours, the production yield does not substantially increase.

On the other hand, after the reaction is completed, a step of purifying the product may be included, if necessary.

Advantageous Effects

As described above, the preparation method according to the present invention has advantages that the production cost can be lowered by using inexpensive starting materials, a high-temperature reaction is not required as a whole, inexpensive and non-explosive reagents are used instead of (trimethylsilyl)diazomethane, and further an intermediate of 4-methoxypyrrole derivatives can be prepared as a whole at a high yield.

DETAILED DESCRIPTION OF THE EMBODIMENTS

Hereinafter, the present invention will be described in more detail with reference to the following examples. However, the following examples are for illustrative purposes only and are not intended to limit the scope of the present invention thereto. On the other hand, in the example and comparative example, the compounds prepared in each step are used in the next steps, and each step can produce more products than those described below for the next step.

Example

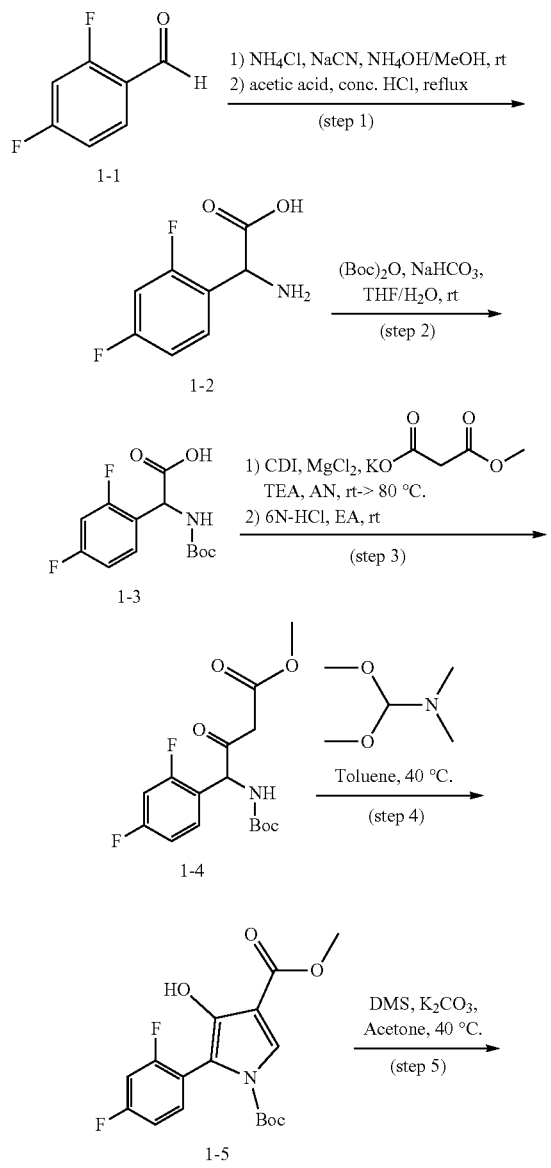

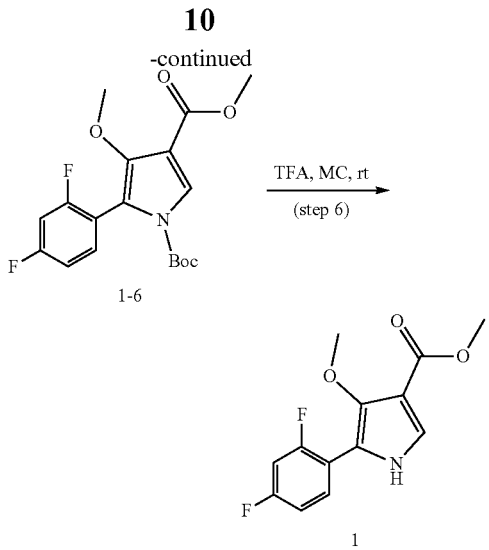

(Step 1)

35.8 g of ammonium chloride and 26.9 g of sodium cyanide were added to a flask, and 716.0 mL of ammonium hydroxide (25 to 28%) was added and then stirred for 10 minutes. The mixture was cooled to 0 to 5° C., stirred for 10 minutes, then heated to room temperature, and stirred for 15 minutes. After cooling to 0 to 5° C., 100.0 g of the prepared 2,4-difluorobenzaldehyde (Chemical Formula 1-1) and 770.0 mL of methanol-containing solution was slowly added to another flask for 15 to 20 minutes. The temperature was raised to room temperature, and the mixture was stirred for 22 hours to complete the first reaction. After concentration under reduced pressure at 50° C., 983.0 mL of acetic acid and 983.0 mL of conc.HCl were added, and refluxed at 100 to 105° C. (internal temperature) for 5 hours to complete the second reaction. It was concentrated under reduced pressure at 75° C., and the solvent was removed until a solid was precipitated. After purified water was added, the crystals were precipitated by stirring. The pH was adjusted to 6.5 using 5M-NaOH solution at internal temperature of 25° C. or less. Ethanol was added thereto and stirred at 10 to 15° C. for 1 hour. After filtration under reduced pressure, the filtrate was washed with ethanol. The resulting solid was dried under reduced pressure to obtain 78.4 g of the compound represented by the Chemical Formula 1-2 (yield: 59.5%).

(Step 2)

100.0 g of the compound represented by the Chemical Formula 1-2 prepared in step 1, 1.5 L of THF and 1.5 L of purified water were added to a flask, and then stirred at room temperature for 10 minutes. The internal temperature was cooled to 0 to 5° C., and 134.6 g of sodium hydrogencarbonate and 139.5 g of di-tert-butyl dicarbonate were added thereto. The mixture was stirred at an internal temperature of 20 to 30° C. for 12 hours to complete the reaction, followed by concentration under reduced pressure at 45° C. After ethyl acetate was added, the internal temperature was cooled to 10° C. or lower. The pH was adjusted to 2.5 using 6N—HCl. The organic layer was separated, dried over anhydrous magnesium sulfate, and concentrated under reduced pressure at 45° C. to obtain 151.2 g of the compound represented by the Chemical Formula 1-3 (yield: 98.5%).

$^1$H-NMR (500 MHz, CDCl$_3$): 8.13-8.14 (d, 1H), 7.37-7.42 (m, 1H), 6.82-6.89 (m, 2H), 5.46-5.47 (d, 1H), 1.23 (s, 9H)

(Step 3)

100.0 g of the compound represented by the Chemical Formula 1-3 prepared in step 2, 61.9 g of carbonyldiimidazole and 1.0 L of acetonitrile were added to a flask, and then stirred at room temperature for 1 hour. 59.8 g of methyl potassium malonate, 36.4 g of anhydrous magnesium chloride, 1.0 L of acetonitrile and 38.8 g of triethylamine were added to another flask and then stirred at 20 to 30° C. for 1 hour. The reactants of the two flasks were mixed and refluxed at an external temperature of 80° C. for 1 hour to complete the reaction. After cooling to room temperature, purified water was added. After cooling the internal temperature to 5 to 10° C., stirring was carried out for 1 hour. The obtained solid was filtered under reduced pressure and washed with purified water. Since the obtained crystal is a magnesium salt, the following salt dissociation process was carried out.

The magnesium salt prepared above, 1.5 L of ethyl acetate and 1.0 L of purified water were added to a flask and stirred for 10 minutes. The pH was adjusted to 7.0 using 6N—HCl. The organic layer was extracted, dried over anhydrous magnesium sulfate, and concentrated under reduced pressure at 45° C. to prepare 97.3 g of the compound represented by the Chemical Formula 1-4 (yield: 81.4%).

$^1$H-NMR (500 MHz, CDCl$_3$): 7.26-7.30 (m, 1H), 6.85-6.92 (m, 2H), 5.83 (s, 1H), 5.64-5.65 (d, 1H), 3.67 (s, 3H), 3.38-3.52 (dd, 2H), 1.41 (s, 9H)

(Step 4)

100.0 g of the compound represented by the Chemical Formula 1-4 prepared in step 3, and 2.0 L of toluene were added to a flask, and then stirred at room temperature for 10 minutes. 104.1 g of N,N-dimethylformamide dimethylacetal was added and stirred at 40° C. for 4 hours to complete the reaction. After concentration under reduced pressure at 45° C., ethyl acetate and purified water were added to the concentrated residue, and then stirred for 10 minutes. The pH was adjusted to 7.0 using 1N—HCl. The organic layer was extracted, dried over anhydrous magnesium sulfate, and then concentrated under reduced pressure at 45° C. to produce 79.2 g of the compound represented by the Chemical Formula 1-5 (yield: 77.0%). On the other hand, the compound represented by the Chemical Formula 1-5 was unstable (aerial oxidation occurred), the following step 5 was continuously carried out by an in-situ process.

$^1$H-NMR (500 MHz, CDCl$_3$): 7.73 (s, 1H), 7.48 (s, 1H), 7.38-7.43 (q, 1H), 6.83-6.95 (tt, 2H), 3.90 (s, 3H), 1.39 (s, 9H)

(Step 5)

100.0 g of the compound represented by the Chemical Formula 1-5 prepared in step 4, and 1.5 L of acetone were added to a flask, and then stirred at room temperature for 10 minutes. 78.2 g of potassium carbonate, and 42.9 g of dimethyl sulfate were added thereto, and then stirred at 40° C. for 6 hours to complete the reaction. After cooling to room temperature, purified water and ethyl acetate were added and stirred for 10 minutes. The pH was adjusted to 7.0 using 6N—HCl. The organic layer was extracted, dried over anhydrous magnesium sulfate, and then concentrated under reduced pressure at 45° C. to obtain 90.6 g of the compound represented by the Chemical Formula 1-6 (yield: 87.1%). Then, the following step 6 was carried out by an in-situ process without further purification.

$^1$H-NMR (500 MHz, CDCl$_3$): 7.87 (s, 1H), 7.31-7.36 (q, 1H), 6.84-6.95 (tt, 2H), 3.86 (s, 3H), 3.68 (s, 3H), 1.38 (s, 9H)

(Step 6)

100.0 g of the compound represented by the Chemical Formula 1-6 prepared in step 5, and 500.0 mL of methylene chloride were added to a flask, and then stirred at room temperature for 10 minutes. 310.4 g of trifluoroacetic acid was added and stirred at room temperature for 6 hours to complete the reaction. After cooling to 0 to 5° C., purified water was slowly added at 15° C. or lower. The pH was adjusted to 7.0 using a 50.0% NaOH solution at 15° C. or lower. Ethyl acetate was added and stirred for 10 minutes. The organic layer was extracted and dried over anhydrous magnesium sulfate. The celite washed with ethyl acetate was placed on a filter, and the organic layer was filtered under reduced pressure and then concentrated under reduced pressure at 45° C. Ethyl acetate was added to the concentrated residue and suspended by stirring. n-Hexane was added thereto, the internal temperature was cooled to 0 to 5° C., and the mixture was stirred for 1 hour. The obtained solid was filtered under reduced pressure. The filtrate was washed with n-hexane, and then dried under reduced pressure to obtain 65.5 g of the compound represented by the Chemical Formula 1 (yield: 90.0%).

$^1$H-NMR (500 MHz, CDCl$_3$): 8.78 (s, 1H), 8.12 (m, 1H), 7.30 (d, 1H), 6.95 (t, 1H), 6.88 (t, 1H), 3.87 (s, 3H), 3.85 (s, 3H)

Comparative Example

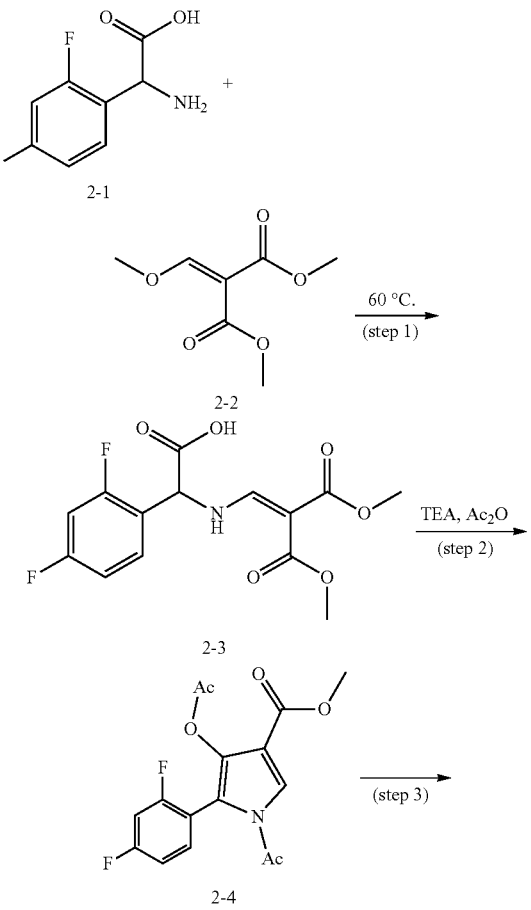

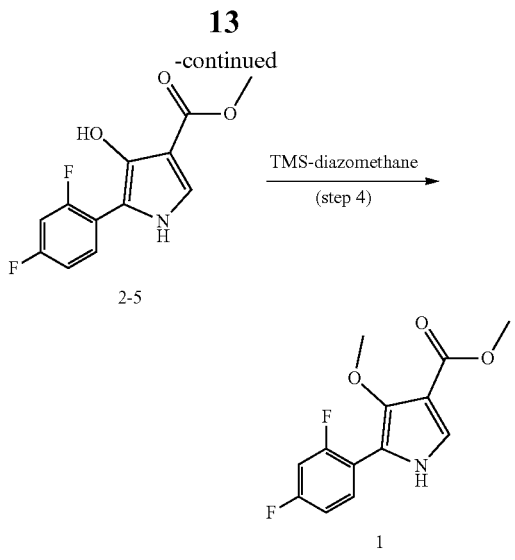

The preparation method was carried out as follows in the same manner as in steps 8-1 to 8-3 of Example 8 of Korean Patent No. 10-1613245.

(Step 1)

2,4-Difluorophenylglycine (Chemical Formula 2-1, 150.0 g, 801.5 mmol), dimethyl 2-(methoxymethylene)malonate (Chemical Formula 2-2, 126.9 g, 728.6 mmol), and sodium acetate (65.8 g, 801.5 mmol) were added to methanol (800.0 ml), and then refluxed at 60° C. for 4 hours. The reaction mixture was cooled to room temperature, and concentrated under reduced pressure to remove about 70% of methanol, and then filtered. The resulting solid was dried under reduced pressure to produce 190.0 g of the compound represented by the Chemical Formula 2-3 (yield: 79.2%).

$^1$H-NMR (500 MHz, CDCl$_3$): 8.02-7.99 (m, 1H), 7.45-7.40 (m, 1H), 7.00-6.95 (m, 2H), 5.16 (s, 1H), 3.74 (s, 3H), 3.76 (s, 3H)

(Step 2)

Acetic anhydride (1731.2 ml) and triethylamine (577.1 ml) were added to the compound represented by the Chemical Formula 2-3 (190.0 g, 577.1 mmol) prepared in step 1. The reaction mixture was refluxed at 140° C. for 30 minutes and then cooled to 0° C. To the reaction mixture, ice water (577.1 ml) was added at 0° C., stirred at room temperature for 1 hour and then extracted with ethyl acetate. The obtained extract was dried over anhydrous magnesium sulfate and then concentrated under reduced pressure. The resulting compound was filtered using a silica gel to remove a solid, and then concentrated under reduced pressure to prepare the compound represented by the Chemical Formula 2-4, which was then used in the following step 3.

(Step 3)

Tetrahydrofuran (140.0 ml) and water (120.0 ml) were added to the resulting residue, cooled to 0° C., followed by addition of sodium hydroxide (46.17 g, 1154.2 mmol). The reaction mixture was stirred at 0° C. for 30 minutes, neutralized using 1N hydrochloric acid aqueous solution and then extracted with ethyl acetate. The obtained extract was dried over anhydrous magnesium sulfate, and then concentrated under reduced pressure. The resulting residue was purified by silica gel column chromatography (ethyl acetate:n-hexane=1:4 (v/v)) to produce 22.0 g of the compound represented by the Chemical Formula 2-5 (yield: 15.1%) (including steps 2 and 3).

$^1$H-NMR (500 MHz, CDCl$_3$): 8.80 (s, 1H), 8.17-8.12 (m, 2H), 7.13 (d, 1H), 6.95 (t, 1H), 6.86-6.83 (m, 1H), 3.88 (s, 3H)

(Step 4)

The compound represented by the Chemical Formula 2-5 (22.0 g, 86.9 mmol) prepared in step 3 was dissolved in tetrahydrofuran (434.5 ml) and methanol (173.9 ml). (Trimethylsilyl)diazomethane (2.0M diethyl ether solution, 173.8 ml) was added to the reaction mixture and then stirred at room temperature for 48 hours. Water was added to the reaction mixture, and extracted with ethyl acetate. The obtained extract was dried over anhydrous magnesium sulfate, and then concentrated under reduced pressure. The resulting residue was purified by silica gel column chromatography (ethyl acetate:n-hexane=1:4 (v/v)) to produce 18.1 g of the compound represented by the Chemical Formula 1 (yield: 75.3%).

$^1$H-NMR (500 MHz, CDCl$_3$): 8.78 (s, 1H), 8.12 (m, 1H), 7.30 (d, 1H), 6.95 (t, 1H), 6.88 (t, 1H), 3.87 (s, 3H), 3.85 (s, 3H)

Comparison of Examples and Comparative Examples

The yields of the preparation methods of the Example and Comparative Example are shown in Table 1 below.

TABLE 1

|  | Example | Comparative Example |
| --- | --- | --- |
| Total yield | 28.8% | 9.0% |
| Total yield from 2,4-difluorophenylglycine to Chemical Formula 1 | 48.4% | 9.0% |

As shown Table 1, it was confirmed that the Example according to the present invention could not only reduce the production cost by using inexpensive aldehyde as a starting material but also improve the yield by about 5.4 times as compared with the Comparative Example.

In particular, both step 2 of Example according to the present invention and step 1 of Comparative Example used 2,4-difluorophenylglycine as a starting material. Comparing the methods for preparing the compound represented by the Chemical Formula 1 from the above step, Example according to the present invention showed a yield of about 50%, whereas Comparative Example showed a yield of 9%, thereby confirming that the yield according to the present invention was remarkably improved.

In addition, in Example according to the present invention, the relatively low temperature was applied in the entire steps, whereas in step 2 of Comparative Example, the reaction temperature of about 140° C. was applied. Thus, the preparation method according to the present invention has an advantage that a relatively low reaction temperature can be applied. Furthermore, step 4 of Comparative Example used (trimethylsilyl)diazomethane which is an explosive reaction material, whereas Example according to the present invention has the advantage that such a reactant was not used.

What is claimed is:

1. A method for preparing a compound represented by the following Chemical Formula 1, comprising the steps of:
   1) reacting a compound represented by the following Chemical Formula 1-1 with ammonium chloride and either sodium cyanide or potassium cyanide, followed by reaction with an acid to prepare a compound represented by the following Chemical Formula 1-2;

2) protecting a compound represented by the following Chemical Formula 1-2 with an amine protecting group (P) to prepare a compound represented by the following Chemical Formula 1-3;

3) reacting a compound represented by the following Chemical Formula 1-3 with (i) methylpotassium malonate or methylsodium malonate, (ii) carbonyldiimidazole, and (iii) magnesium halide, followed by reaction with an acid to prepare a compound represented by the following Chemical Formula 1-4;

4) reacting a compound represented by the following Chemical Formula 1-4 with N,N-dimethylformamide dimethylacetal to prepare a compound represented by the following Chemical Formula 1-5;

5) reacting a compound represented by the following Chemical Formula 1-5 with dimethyl sulfate to prepare a compound represented by the following Chemical Formula 1-6; and 6) reacting a compound represented by the following Chemical Formula 1-6 with an acid to prepare a compound represented by the following Chemical Formula 1:

[Chemical Formula 1]

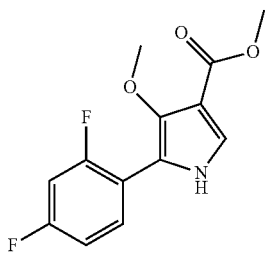

[Chemical Formula 1-1]

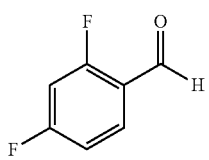

[Chemical Formula 1-2]

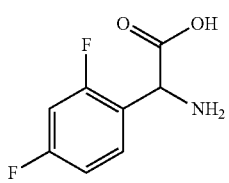

[Chemical Formula 1-3]

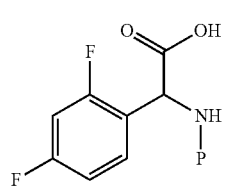

[Chemical Formula 1-4]

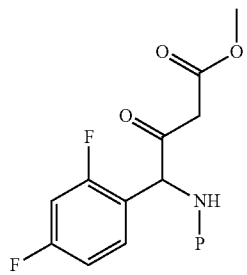

[Chemical Formula 1-5]

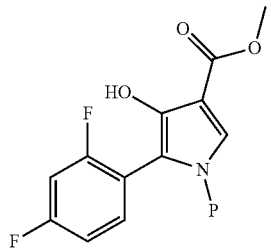

[Chemical Formula 1-6]

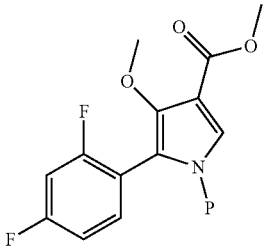

2. The method according to claim 1, wherein in the step 1, a molar ratio of the compound represented by the Chemical Formula 1-1 to ammonium chloride is 10:1 to 1:10 and a molar ratio of the compound represented by the Chemical Formula 1-1 to sodium cyanide or potassium cyanide is 10:1 to 1:10.

3. The method according to claim 1, wherein in the step 1, the reaction with the compound represented by the Chemical Formula 1-1, ammonium chloride and either sodium cyanide or potassium cyanide is carried out at 0° C. to 40° C., and the reaction with an acid is carried out at 80° C. to 120° C.

4. The method according to claim 1, wherein the acid in the step 1 is either acetic acid or hydrochloric acid.

5. The method according to claim 1, wherein the amine protecting group (P) in the step 2 is either tert-butoxycarbonyl, fluorenylmethyloxycarbonyl, Tosyl, or Acyl.

6. The method according to claim 1, wherein the reaction of the step 2 is carried out at 10° C. to 40° C.

7. The method according to claim 1, wherein the magnesium halide in the step 3 is either magnesium chloride or magnesium bromide.

8. The method according to claim 1, wherein in the step 3, a molar ratio of the compound represented by the Chemical Formula 1-3 to methylpotassium malonate or methylsodium malonate is 10:1 to 1:10, a molar ratio of the compound represented by the Chemical Formula 1-3 to carbonyldiimidazole is 10:1 to 1:10, and a molar ratio of the compound represented by the Chemical Formula 1-3 to the magnesium halide is 10:1 to 1:10.

9. The method according to claim 1, wherein the acid in the step 3 is either hydrochloric acid, nitric acid, sulfuric acid, or phosphoric acid.

10. The method according to claim 1, wherein the reaction between the compound represented by the Chemical Formula 1-3 and (i) methylpotassium malonate or methylsodium malonate, (ii) carbonyldiimidazole, and (iii) magnesium halide in the step 3 is carried out at 50° C. to 100° C., and the reaction with the acid is carried out at 0° C. to 40° C.

11. The method according to claim 1, wherein a molar ratio of the compound represented by the Chemical Formula 1-4 to N,N-dimethylformamide dimethylacetal in the step 4 is 1:1 to 1:10.

12. The method according to claim 1, wherein the reaction of the step 4 is carried out at 20° C. to 70° C.

13. The method according to claim 1, wherein a molar ratio of the compound represented by the Chemical Formula 1-5 to dimethylsulfate in the step 5 is 10:1 to 1:10.

14. The method according to claim 1, wherein the reaction of the step 5 is carried out at 20° C. to 60° C.

15. The method according to claim 1, wherein the acid in the step 6 is trifluoroacetic acid and a molar ratio of the compound represented by the Chemical Formula 1-6 to the trifluoroacetic acid in the step 6 is 1:1 to 1:30.

16. The method according to claim 1, wherein the reaction of the step 6 is carried out at 10° C. to 40° C.

17. The method according to claim 1, wherein the acid of the step 6 is either trifluoroacetic acid, hydrochloric acid, nitric acid, sulfuric acid, or phosphoric acid.

* * * * *